US006716452B1

(12) United States Patent
Piccariello et al.

(10) Patent No.: US 6,716,452 B1
(45) Date of Patent: Apr. 6, 2004

(54) ACTIVE AGENT DELIVERY SYSTEMS AND METHODS FOR PROTECTING AND ADMINISTERING ACTIVE AGENTS

(75) Inventors: Thomas Piccariello, Blacksburg, VA (US); Lawrence P. Olon, Bristol, TN (US); Randall J. Kirk, Radford, VA (US)

(73) Assignee: New River Pharmaceuticals Inc., Redford, VA (US)

( * ) Notice: Subject to any disclaimer, the term of this patent is extended or adjusted under 35 U.S.C. 154(b) by 0 days.

(21) Appl. No.: 09/642,820

(22) Filed: Aug. 22, 2000

(51) Int. Cl.⁷ .............................. A61K 9/22; A61K 9/52; A61K 38/02; A61K 47/42
(52) U.S. Cl. ......................... 424/457; 424/468; 514/2; 530/300; 530/345
(58) Field of Search ................................. 424/426, 457, 424/460, 468, 486, 499; 514/2; 530/333, 338, 342, 300, 345, 405, 409; 426/648

(56) References Cited

U.S. PATENT DOCUMENTS

| 3,331,814 A | 7/1967 | Randall .................... 528/327 |
| 3,846,399 A | * 11/1974 | Hirschmann et al. |
| 3,975,342 A | 8/1976 | Gross ....................... 530/363 |

(List continued on next page.)

FOREIGN PATENT DOCUMENTS

| EP | 0 187 547 A2 | 7/1986 |
| WO | WO 95/12605 | 5/1995 |
| WO | WO 95/14033 | 5/1995 |
| WO | WO 97/21993 A2 | 6/1997 |
| WO | WO 97/36616 | 10/1997 |
| WO | WO-98/04277 A1 | * 2/1998 |

OTHER PUBLICATIONS

Okada et al. Synthesis of Glycopeptide Conjugates . . . Proc. Japan Academy, vol. 73, Ser. B. No. 10, pp. 205–209, Dec. 1997.*

Canaris, G., "The Colorado Thyroid Disease Prevalence Study," *Archives Internal Medicine Articles and Abstracts*, vol. 160, No. 4 (2000).

Bunevicius, R., "Effects of Thyroxine as Compared with Thyroxine Plus Triiodothyronine in Patients with Hypothyroidism," *The New England Journal of Medicine*, vol. 340, No. 6 (1999).

Toft, A., "Thyroid Hormone Replacement—One Hormone or Two?," *The New England Journal of Medicine*, vol. 340, No. 6 (1999).

Pade, V., et al., "Link Between Drug Adsorption Solubility and Permeability Measurements In Caco–2 Cells," *Journal of Pharmaceutical Sciences*, vol. 87, No. 12 (1998).

Oh, D., et al., "Estimating the Fraction Dose Absorbed from Suspensions of Poorly Soluble Compounds in Humans: A Mathematical Model," *Pharmaceutical Research*, vol. 10, No. 2 (1993).

Amidon, G., et al., "A Theoretical Basis for a Biopharmaceutic Drug Classification: The Correlation of in Vitro Drug Product Dissolution and in Vivo Bioavailability," *Pharmaceutical Research*, vol. 12, No. 3 (1995).

(List continued on next page.)

*Primary Examiner*—Jeffrey E. Russel
(74) *Attorney, Agent, or Firm*—Hunton & Willaims LLP

(57) ABSTRACT

A composition comprising a polypeptide and an active agent covalently attached to the polypeptide. Also provided is a method for delivery of an active agent to a patient comprising administering to the patient a composition comprising a polypeptide and an active agent covalently attached to the polypeptide. Also provided is a method for protecting an active agent from degradation comprising covalently attaching the active agent to a polypeptide. Also provided is a method for controlling release of an active agent from a composition comprising covalently attaching the active agent to the polypeptide.

64 Claims, 5 Drawing Sheets

U.S. PATENT DOCUMENTS

| | | | |
|---|---|---|---|
| 3,998,799 A | 12/1976 | Bodor et al. | 560/257 |
| 4,040,907 A | 8/1977 | Ullman et al. | 435/188 |
| 4,224,316 A | 9/1980 | Momany | 514/17 |
| 4,297,346 A | 10/1981 | Rips et al. | 514/19 |
| 4,356,166 A | 10/1982 | Peterson et al. | 424/19 |
| 4,358,604 A | 11/1982 | Albarella et al. | 560/40 |
| 4,399,121 A | 8/1983 | Albarella et al. | 530/363 |
| 4,426,453 A | 1/1984 | Cree et al. | 436/500 |
| 4,427,660 A | 1/1984 | Schiffman et al. | 514/18 |
| 4,457,907 A * | 7/1984 | Porter | 424/10.3 |
| 4,483,807 A | 11/1984 | Asano et al. | 264/22 |
| 4,490,221 A | 12/1984 | Collange et al. | 204/72 |
| 4,552,864 A | 11/1985 | Antoni et al. | 514/15 |
| 4,569,844 A | 2/1986 | Jones | 426/2 |
| 4,650,675 A | 3/1987 | Borel et al. | 424/179.1 |
| 4,657,873 A | 4/1987 | Gadow et al. | 436/532 |
| 4,753,804 A | 6/1988 | Iaccheri et al. | 424/491 |
| 4,766,121 A | 8/1988 | Ellis et al. | 514/247 |
| 4,801,575 A | 1/1989 | Pardridge | 514/4 |
| 4,863,735 A | 9/1989 | Kohn et al. | 424/422 |
| 4,902,505 A | 2/1990 | Pardridge et al. | 424/85.7 |
| 4,925,673 A | 5/1990 | Steiner et al. | 424/455 |
| 4,960,790 A | 10/1990 | Stella et al. | 514/449 |
| 4,976,962 A | 12/1990 | Bichon et al. | 424/424 |
| 5,057,317 A | 10/1991 | Iida | 424/423 |
| 5,073,641 A | 12/1991 | Bundgaard et al. | 560/56 |
| 5,087,616 A * | 2/1992 | Myers et al. | 514/21 |
| 5,169,933 A | 12/1992 | Anderson et al. | 530/391.3 |
| 5,219,564 A | 6/1993 | Zalipsky et al. | 424/78.17 |
| 5,225,204 A | 7/1993 | Chen et al. | 424/484 |
| 5,238,714 A * | 8/1993 | Wallace et al. | 427/213.36 |
| 5,324,522 A | 6/1994 | Krenning et al. | 424/456 |
| 5,362,831 A | 11/1994 | Mongelli et al. | 526/304 |
| 5,451,410 A | 9/1995 | Milstein et al. | 424/490 |
| 5,534,496 A | 7/1996 | Lee et al. | 514/17 |
| 5,643,957 A | 7/1997 | Leone-Bay et al. | 514/563 |
| 5,670,477 A | 9/1997 | Poduslo et al. | 514/2 |
| 5,707,979 A | 1/1998 | Peyman et al. | 514/110 |
| 5,741,705 A | 4/1998 | Blom et al. | 435/348 |
| 5,756,291 A | 5/1998 | Griffin et al. | 435/6 |
| 5,762,909 A | 6/1998 | Uzgiris | 424/9.34 |
| 5,767,227 A | 6/1998 | Latham et al. | 530/324 |
| 5,776,885 A | 7/1998 | Orsolini et al. | 514/2 |
| 5,792,451 A | 8/1998 | Sarubbi et al. | 424/85.4 |
| 5,820,881 A | 10/1998 | Milstein | 424/489 |
| 5,846,743 A | 12/1998 | Janmey et al. | 435/7.8 |
| 5,851,536 A | 12/1998 | Yager et al. | 424/400 |
| 5,861,387 A | 1/1999 | Labrie et al. | 514/169 |
| 5,882,645 A * | 3/1999 | Toth et al. | 424/194.1 |
| 5,891,459 A * | 4/1999 | Cooke et al. | 424/439 |
| 5,891,478 A | 4/1999 | Johnson et al. | 424/502 |
| 5,898,033 A * | 4/1999 | Swadesh et al. | 514/224.2 |
| 5,910,569 A | 6/1999 | Latham et al. | 530/324 |
| 5,935,995 A | 8/1999 | Bosslet et al. | 514/460 |
| 5,948,750 A * | 9/1999 | Garsky et al. | 514/2 |
| 5,952,294 A | 9/1999 | Lazo et al. | 514/2 |
| 5,955,105 A | 9/1999 | Mitra et al. | 424/464 |
| 5,977,163 A | 11/1999 | Li et al. | 514/449 |
| 6,005,004 A * | 12/1999 | Katz et al. | 514/549 |
| 6,030,941 A * | 2/2000 | Summerton et al. | 514/2 |
| 6,043,230 A | 3/2000 | Arimilli et al. | 514/81 |
| 6,048,736 A | 4/2000 | Kosak | 436/556 |
| 6,074,659 A | 6/2000 | Kunz et al. | 424/423 |
| 6,093,391 A | 7/2000 | Kabanov et al. | 424/85.1 |
| 6,146,658 A | 11/2000 | Bosslet et al. | 424/450 |
| 6,306,993 B1 | 10/2001 | Rothbard et al. | 526/304 |
| 6,355,666 B1 | 3/2002 | Lai et al. | 514/411 |
| 6,429,223 B1 | 8/2002 | Lai et al. | 514/411 |
| 6,458,842 B1 | 10/2002 | Dickinson et al. | 514/567 |
| 2002/0098999 A1 | 7/2002 | Gallop et al. | 514/1 |
| 2002/0151526 A1 | 10/2002 | Gallop et al. | 514/143 |
| 2002/0151529 A1 | 10/2002 | Cundy et al. | 514/169 |

OTHER PUBLICATIONS

Presentation to Knoll Pharmaceutical, Apr. 10, 2000.
Investment Banking Presentation, Mar. 27–31, 2000.
Pharma Presentation, Mar. 27–31, 2000, New York, NY.
Deutsche Banc Alex Brown 2000 Health Care Conference Presentation, May 10, 2000, Baltimore, MD.
Apr. 7, 2000, Letter to Credit Suisse First Boston Corporation.
Apr. 7, 2000, Letter to Chase, Hambrecht and Quist.
Apr. 7, 2000, Letter to Banc of America Securities, LLC.
Apr. 7, 2000, Letter to Johnson & Johnson.
Apr. 7, 2000, Letter to AstraZeneca LP.
Apr. 7, 2000, Letters to Bear, Stearns & Company, Inc.
Bankers Presentation, Mar. 27–31, 2000.
Pharmaceutical Presentation, Mar. 27–31, 2000.
KPMG Auditors' Report, Mar. 12, 1999.
Final Report, Study Completion Date Jun. 25, 1998.
Investment Banking Presentation, Mar. 27–31, 2000.
Pharmaceutical Presentation, Mar. 27–31, 2000.
Deutsche Banc Alex Brown 2000 Health Care Conference Presentation, May 10, 2000, Baltimore, MD.
Investment Banking (short) Presentation, Apr. 27, 2000.
Investment Banking (long) Presentation, Apr. 27, 2000.
Banc of America Presentation, (not dated).
Pharma Presentation, Apr. 2000.
AstraZeneca Presentation, (not dated).
"Promise of Polythroid," Presentation, Mar. 2000.
"Introducing Polythroid," Presentation, Mar. 2000.
Investment Banking Presentation, (not dated).
Pharma Presentation, Mar.–Apr., (no year given).
Deutsche Banc Alex Brown 2000.
Aug. 31, 1999 Presentation to Scios, Inc.
Feb. 2000 Presentation to Andrx.
Mar. 15, 2000 Presentation to BASF.
Original Presentation to BASF, (not dated).
Feb. 10, 2000 Lotus Presentation.
Orten, James M. et al., "Thyroxine," *Human Biochemistry*, 9th Ed.. C.V. Mosby Company, St. Louis,pp. 401–405 (1975).
Li, Chun, et al., "Complete Regression of Well–Established Tumors Using a Novel Water–Soluble Poly(L–Glutamic Acid)–Paclitaxel Conjugate," *Cancer Res*, 58:2404–2409 (1998).
Kramer, Werner et al., "Intestinal Absorption of Peptides by Coupling to Bile Acids," *The Journal of Biological Chemistry*, 269(14):10621–10627 (1994).
Rawitch, Allen B., et al., "The Isolation of Identical Thyroxine Containing Amino Acid Sequences from Bovine, Ovine and Porcine Thyroglobulins," *Biochemical and Biophysical Research Communications*, 118(2):423–429 (1984).
Marriq, Claudine, et al., "Amino Acid Sequence of the Unique 3,5,3'–Triiodothyronine–Containing Sequence from Porcine Thyroglobulin," *Biochemical and Biophysical Research Communications*, 112(1):206–213 (1983).
Sawada, Kyoko, et al., "Recognition of L–Amino Acid Ester Compounds by Rat Peptide Transporters PEPT1 and PEPT2," *Journal of Pharmacology and Experimental Therapeutics*, 291(2):705–709 (1999).

De Vrueh, Remco L.A., et al, "Transport of L–Valine–Acyclovir Via the Oligopeptide Transporter in the Human Intestinal Cell Line, Caco–2," *Journal of Pharmacology and Experimental Therapeutics*, 286(2):1166–1170 (1988).

Guo, Allan, et al., "Interactions of a Nonpeptide Drug, Valacyclovir, with the Human Intestinal Peptide Transporter (hPEPT1) Expressed in a Mammalian Cell Line," *Journal of Pharmacology and Experimental Therapeutics*, 289(1):448–454 (1999).

Burnette, Thimysta C., et al., "Metabolic Disposition of the Acyclovir Prodrug Valaciclovir in the Rat," *Drug Metabolism and Disposition*, 22(1):60–64 (1994).

Aggarwal, et al., "Synthesis and Biological Evaluation of Prodrugs of Zidovudine," *J. Med. Chem.*, 33(5):1505–1511 (1990).

Zunino, Franco, et al., "Comparison of Antitumor Effects of Daunorubicin Covalently Linked to Poly–L–Amino Acid Carriers," *European Journal of Cancer & Clinical Oncology*, 20(3):121–125 (1984).

Havranova, Marie et al., "A High–Molecular Mass Derivative of Trypsin–Kallikrein Inhibitor for Potential Medical Use, II," *Hoppe–Seyler's Z. Physiol. Chem.*, 363:295–303 (1982).

Ryser, Hugues J.P., et al., "Conjugation of Methotrexate to Poly (L–lysine) Increases Drug Transport and Overcomes Drug Resistance in Cultured Cells," *Proc. Natl. Acad. Sci. USA*, 75(8):3867–3870 (1978).

Han, Hyo–Kyung, et al., "Targeted Prodrug Design to Optimize Drug Delivery," *AAPS PharmSci*, 2(1): Article 6 (2000).

Tamai, I., et al., "Improvement of L–dopa Absorption by Dipeptidyl Derivation, Utilizing Peptide Transporter PepT1," *J. Pharma. Sci.*, 87(12):1542–1546 (1988), Abstract.

Werner Kramer, et al., *Intestinal Absorption of Peptides by Coupling to Bile Acids*, The Journal of Biological Chemistry, vol. 269, No. 14, pp. 10621–10627 (Apr. 8, 1994).

Brigitte Schmidt, et al., *Peptide–Linked 1,3–Dialkyl 1–3–acyltriazenes: Gastrin Receptor Directed Antineoplastic Alkylating Agents*, Journal of Medicinal Chemistry, vol. 37, No. 22, pp. 3812–3817 (1994).

Kovacs, J., "Glutamic and Aspartic Anhydrides. Rerrangement of N–Carboxyglutamic 1,5–Anhydride to the Leuchs' Anhydride and Conversion of the Latter to Pyroglutamic Acid," 85:1839–1844, (Jun. 20, 1963).

Zunino, Franco, et al., "Anti–Tumor Activity of Daunorubicin Linked to Poly L–Aspartic Acid," *Int. J. Cancer*, 30:465–470 (1982).

Okada, Masahiko, et al., "Synthesis ofGlycopeptide–Conjugates via Ring–Opening Polymerization of Sugar–Substituted α–Amino Acid N–Carboxyanhydrides (GlycoNCAs)," *Proc. Japan Acad.*, 73:205–209, (1997).

Nishida, Koyo, et al., "Pharmacokinetic Analysis of in Vivo Metabolism of Amino Acid or Dipeptide Conjugates ofSalicylic Acid in Rabbit Intestinal Microorganisms," *Pharmaceutical Research*, 11(1):160–164 (1994).

Schmidt, Brigitte F., et al., "Peptide–Linked 1,3–Dialkyl–3–acyltriazenes: Gastrin Receptor Directed Antineoplastic Alkylating Agents," *Journal of Medicinal Chemistry* 37(22):3812–3817 (1994).

Kawai, Tohru, et al., "Direct Polymerization of N–Carboxy Anhydride of L–Glutamic Acid," *Makromol. Chem.*, 182:2127–2137 (1981).

Oh, DM, et al., "Drug Transport and Targeting. Intestinal Transport," *Pharma Biotechnol*, 12:59–88 (1999), Abstract.

Balimane, P., et al., "Effect of Ionization on the Variable Uptake of Valacyclovir via the Human Intestinal Peptide Transporter (hPepT1) in CHP cells," *Biopharm Drug Dispos*, 21(5):165–174 (2000), Abstract.

Knutter, I, et al., "A Novel Inhibitor of the Mammalian Peptide Transporter PEPT1," *Biochemistry*, 40(14):4454–4458 (2001), Abstract.

Shen, H., et al., "Developmental Expression of PEPT1 and PEPT2 in Rat Small Intestine, Colon, and Kidney," *Pediatr Res*, 49(6):789–795 (2001), Abstract.

Friedrichsen, G.M., et al., "Model Prodrugs Designed for the Intestinal Peptide Transporter. A Synthetic Approach for Coupling of Hydroxy–Containing Compounds to Dipeptides," *Eur J Pharm Sci*, 14(1):13–19 (2001, Abstract).

Han H., et al., "5'–Amino Acid Esters of Antiviral Nucleosides, Acyclovir, and AZT and Aborbed by the Intestinal PEPT1 Peotide Transporter," *Pharm Res*, 15(8):1154–1159 (1998), Abstract.

Blimane, P.V., et al., "Direct Evidence for Peptide Transporter (PepT1)–Mediated Uptake of a Nonpeptide Prodrug, Valcyclovir," *Biochem Biophys Res Commun*, 250(2):246–251 (1998), Abstract.

Han, H.K., et al., "Cellular Uptake Mechanism of Amino Acid Ester prodrugs in Caco–2hPEPT1 Cells Overexpressing a Human Peptide Transporter," *Pharm Res*, 15(9):1382–1386 (1998), Abstract.

Shiraga, T., et al., "Cellular and Molecular Mechanisms of Dietary Regulation on Rat Intestinal $H_+$/Peptide Transporter PepT1," *Gastroenterology*, 116(2):354–362 (1999), Abstract.

Guo, A., et al., "Interactions of a Nonpeptidic Drug, Valacyclovir, with the Human Intestinal Peptide Transporter (hPEPT1) Expressed in a Mammalian Cell Line," *Pharmacol Exp Ther*, 269(1):448–454 (1999), Abstract.

Amidon, G.L., et al., "5'–Amino Acid Esters of Antiviral Nucleosides, Acyclovir, and AZT are Absorbed by the Intestinal PEPT1 Peptide Transporter," *Pharm Res* 16(2):175 (1999), Abstract.

Leibach, F.H, et al., "Peptide Transporters in the Intestine and the Kidney," *Annu Rev Nutri*, 16:99–119 (1996), Abstract.

Herrera–Ruiz, D.; et al., "Spatial Expression Patterns of Peptide Transporters in the Human and Rat Gastrointestinal Tracts, Caco–2 in vitro Cell Culture Model, and Multiple Human Tissues," *AAPS PharmSci*, 3(1):E9 (2001), Abstract.

Toth, Istvan, "A Novel Chemical Approach to Drug Delivery: Lipidic Amino Acid Conjugates," *Journal of Drug Targeting*, 2:217–239 (1994).

Naoki Negishi, et al., "Coupling of Naltrexone to Biodegradable Poly (α–Amino Acids)," *Pharmaceutical Research*, 4(4):305–310 (1987).

Bennett, R., et al., "O–Phosphoric Acid Esters of 3,5–Diiodotyrosine and Thyroxine," *Journal of Medicinal and Pharmaceutical Chemistry*, 2(5):493–498 (1960).

Greene, Theodora, et al., "Protection for Phenols," *Protective Groups in Organic Synthesis*, $2^{nd}$ Ed., John Wiley & Sones, Inc., (1991).

Hoffenberg, R., et al., "The Application of Mass Spectrometry to the Study of Thyroxine and Related Compounds in Biological Fluids," *Mass Spectrometry in Biochemistry and Medicine*, pp. 303–312 (1974).

Perisico, F.J., et al., "Effect of Tolmetin Glycine Amide (McN–4366), a Prodrug of Tolmetin Sodium, on Adjuvant Arthritis in the Rat," *The Journal of Pharmacology and Experimental Therapeutics*, 247(3):889–896 (1986).

Smith, Richard H., et al., "1,3–Dimethyl–3–acyltriazenes: Synthesis and Chemistry of a Novel Class of Biological Methylating Agents," *J. Org. Chem.* 51(20):3751–3757 (1986).

Smith, R. H., et al., "1,3–Dialkyl–3–acyltriazenes, A Novel Class of Antineoplastic Alkylating Agents," *Journal of Medicinal Chemistry*, 33(9):25792583 (1990).

Ueki, Masaki, et al., Methylphosphinyl (Omp): A New Protecting Group of Tyrosine Suitable for Peptide Synthesis by Use of Boc–Amino Acids,I *Tetrahedron Letters*, 27(35):4181–4184 (1986).

Makoto, Iwatsuki, it al., "Beta2 Microglobulin Adsorbent," (Abstract of JP04126160), (Apr. 27, 1992).

Toru, Kawai, et al., "Gamma–Glutamic Acid N–Carboxyanhydride," (Abstract of JP52100486). (Aug. 23, 1997).

Nariyoshi, Ebihara, et al., "Polyamino Acid Block Copolymer and Preparation Thereof," (Abstract of JP55145736). (Nov. 13, 1980).

Bennett, Raymond, et al., "O–Phosphoric Acid Esters of 3,5–Diiodotyrosine and Thyroxine," *Chemical Abstracts*, 55(9):8303 (1961).

* cited by examiner

Acid Drug/N-Terminus Scheme

R'=Radical moiety attached to acid functionality on drug
R=Side chain of amino acid or peptide
HOBt=Hydroxybenzotriazole
DIPC=Diisopropylcarbodiimide Amine Drug/C-Terminus Scheme R'=Radical moiety attached to amine functionality on drug
R=Side chain of amino acid or peptide
HOBt=Hydroxybenzotriazole
DIPC=Diisopropylcarbodiimide

Alcohol Drug/N-Terminus Scheme

R'=Radical moiety attached to alcohol functionality on drug
R=Side chain of amino acid or peptide Mechanism of Alcohol Drug From
Glutamic Acid Dimer Scheme R'=Radical moiety attached to alcohol functionality on drug
R=Side chain of amino acid or peptide

ACTIVE AGENT DELIVERY SYSTEMS AND METHODS FOR PROTECTING AND ADMINISTERING ACTIVE AGENTS

FIELD OF THE INVENTION

The present invention relates to active agent delivery systems and, more specifically, to compositions that comprise polypeptides covalently attached to active agents and methods for protecting and administering active agents.

BACKGROUND OF THE INVENTION

Active agent delivery systems are often critical for the effective delivery of a biologically active agent (active agent) to the appropriate target. The importance of these systems becomes magnified when patient compliance and active agent stability are taken under consideration. For instance, one would expect patient compliance to increase markedly if an active agent is administered orally in lieu of an injection or another invasive technique. Increasing the stability of the active agent, such as prolonging shelf life or survival in the stomach, will assure dosage reproducibility and perhaps even reduce the number of dosages required which could improve patient compliance.

Absorption of an orally administered active agent is often blocked by the harshly acidic stomach milieu, powerful digestive enzymes in the GI tract, permeability of cellular membranes and transport across lipid bilayers. Incorporating adjuvants such as resorcinol, surfactants, polyethylene glycol (PEG) or bile acids enhance permeability of cellular membranes. Microencapsulating active agents using protenoid microspheres, liposomes or polysaccharides have been effective in abating enzyme degradation of the active agent. Enzyme inhibiting adjuvants have also been used to prevent enzyme degradation. Enteric coatings have been used as a protector of pharmaceuticals in the stomach.

Active agent delivery systems also provide the ability to control the release of the active agent. For example, formulating diazepam with a copolymer of glutamic acid and aspartic acid enables a sustained release of the active agent. As another example, copolymers of lactic acid and glutaric acid are used to provide timed release of human growth hormone. A wide range of pharmaceuticals purportedly provide sustained release through microencapsulation of the active agent in amides of dicarboxylic acids, modified amino acids or thermally condensed amino acids. Slow release rendering additives can also be intermixed with a large array of active agents in tablet formulations.

Each of these technologies imparts enhanced stability and time-release properties to active agent substances. Unfortunately, these technologies suffer from several shortcomings. Incorporation of the active agent is often dependent on diffusion into the microencapsulating matrix, which may not be quantitative and may complicate dosage reproducibility. In addition, encapsulated drugs rely on diffusion out of the matrix, which is highly dependant on the water solubility of the active agent. Conversely, water-soluble microspheres swell by an infinite degree and, unfortunately, may release the active agent in bursts with little active agent available for sustained release. Furthermore, in some technologies, control of the degradation process required for active agent release is unreliable. For example, an enterically coated active agent depends on pH to release the active agent and, as such, is difficult to control the rate of release.

In the past, use has been made of amino acid side chains of polypeptides as pendant groups to which active agents can be attached. These technologies typically require the use of spacer groups between the amino acid pendant group and the active agent. The peptide-drug conjugates of this class of drug delivery system rely on enzymes in the bloodstream for the release of the drug and, as such, are not used for oral administration. Examples of timed and targeted release of injectable or subcutaneous pharmaceuticals include: linking of norethindrone, via a hydroxypropyl spacer, to the gamma carboxylate of polyglutamic acid; and linking of nitrogen mustard, via a peptide spacer, to the gamma carbamide of polyglutamine. Dexamethasone has been covalently attached directly to the beta carboxylate of polyaspartic acid without a spacer group. This prodrug formulation was designed as a colon-specific drug delivery system where the drug is released by bacterial hydrolytic enzymes residing in the large intestines. The released dexamethasone active agent, in turn, was targeted to treat large bowel disorders and was not intended to be absorbed into the bloodstream. Yet another technology combines the advantages of covalent drug attachment with liposome formation where the active ingredient is attached to highly ordered lipid films (known as HARs) via a peptide linker. Thus, there has been no drug delivery system, heretofore reported, that incorporates the concept of attaching an active ingredient to a polypeptide pendant group with its targeted delivery into the bloodstream via oral administration.

It is also important to control the molecular weight, molecular size and particle size of the active agent delivery system. Variable molecular weights have unpredictable diffusion rates and pharmacokinetics. High molecular weight carriers are digested slowly or late, as in the case of naproxen-linked dextran, which is digested almost exclusively in the colon by bacterial enzymes. High molecular weight microspheres usually have high moisture content which may present a problem with water labile active ingredients. Particle size not only becomes a problem with injectable drugs, as in the HAR application, but absorption through the brush-border membrane of the intestines is limited to less than 5 microns.

SUMMARY OF THE INVENTION

The present invention provides covalent attachment of active agents to a polymer of peptides or amino acids. The invention is distinguished from the above mentioned technologies by virtue of covalently attaching the active agent, which includes, for example, pharmaceutical drugs and nutrients, to the N-terminus, the C-terminus or directly to the amino acid side chain of an oligopeptide or polypeptide, also referred to herein as a carrier peptide. In certain applications, the polypeptide will stabilize the active agent, primarily in the stomach, through conformational protection. In these applications, delivery of the active agent is controlled, in part, by the kinetics of unfolding of the carrier peptide. Upon entry into the upper intestinal tract, indigenous enzymes release the active ingredient for absorption by the body by selectively hydrolyzing the peptide bonds of the carrier peptide. This enzymatic action introduces a second order sustained release mechanism.

The invention provides a composition comprising a polypeptide and an active agent covalently attached to the polypeptide. Preferably, the polypeptide is (i) an oligopeptide, (ii) a homopolymer of one of the twenty naturally occurring amino acids, (iii) a heteropolymer of two or more naturally occurring amino acids, (iv) a homopolymer of a synthetic amino acid, (v) a heteropolymer of two or more synthetic amino acids or (vi) a heteropolymer of one or more naturally occurring amino acids and one or more synthetic amino acids.

The active agent preferably is covalently attached to a side chain, the N-terminus or the C-terminus of the polypeptide. In a preferred embodiment, the active agent is a carboxylic acid and is covalently attached to the N-terminus of the polypeptide. In another preferred embodiment, the active agent is an amine and is covalently attached to the C-terminus of the polypeptide. In another preferred embodiment, the active agent is an alcohol and is covalently attached to the C-terminus of the polypeptide. In yet another preferred embodiment, the active agent is an alcohol and is covalently attached to the N-terminus of the polypeptide.

The composition of the invention can also include one or more of a microencapsulating agent, an adjuvant and a pharmaceutically acceptable excipient. The microencapsulating agent can be selected from polyethylene glycol (PEG), an amino acid, a sugar and a salt. When an adjuvant is included in the composition, the adjuvant preferably activates an intestinal transporter.

Preferably, the composition of the invention is in the form of an ingestable tablet, an intravenous preparation or an oral suspension. The active agent can be conformationally protected by folding of the polypeptide about the active agent. In another embodiment, the polypeptide is capable of releasing the active agent from the composition in a pH-dependent manner.

The invention also provides a method for protecting an active agent from degradation comprising covalently attaching the active agent to a polypeptide.

The invention also provides a method for controlling release of an active agent from a composition wherein the composition comprises a polypeptide, the method comprising covalently attaching the active agent to the polypeptide.

The invention also provides a method for delivering an active agent to a patient, the patient being a human or a non-human animal, comprising administering to the patient a composition comprising a polypeptide and an active agent covalently attached to the polypeptide. In a preferred embodiment, the active agent is released from the composition by an enzyme-catalyzed release. In another preferred embodiment, the active agent is released in a time-dependent manner based on the pharmacokinetics of the enzyme-catalyzed release. In another preferred embodiment, the composition further comprises a microencapsulating agent and the active agent is released from the composition by dissolution of the microencapsulating agent. In another preferred embodiment, the active agent is released from the composition by a pH-dependent unfolding of the polypeptide. In another preferred embodiment, the active agent is released from the composition in a sustained release. In yet another preferred embodiment, the composition firer comprises an adjuvant covalently attached to the polypeptide and release of the adjuvant from the composition is controlled by the polypeptide. The adjuvant can be microencapsulated into a carrier peptide-drug conjugate for biphasic release of active ingredients.

The invention also provides a method for preparing a composition comprising a polypeptide and an active agent covalently attached to the polypeptide. The method comprises the steps of:
  (a) attaching the active agent to a side chain of an amino acid to form an active agent/amino acid complex;
  (b) forming an active agent/amino acid complex N-carboxyanhydride (NCA) from the active agent/amino acid complex; and
  (c) polymerizing the active agent/amino acid complex N-carboxyanhydride (NCA).

In a preferred embodiment, the active agent is a pharmaceutical agent or an adjuvant in another preferred embodiment, steps (a) and (b) are repeated prior to step (c) with a second active agent. When steps (a) and (b) are repeated prior to step (c) with a second agent, the active agent and second active agent can be copolymerized in step (c). In another preferred embodiment, the amino acid is glutamic acid and the active agent is released from the glutamic acid as a dimer upon a hydrolysis of the polypeptide and wherein the active agent is released from the glutamic acid by coincident intramolecular transamination. In another preferred embodiment, the glutamic acid is replaced by an amino acid selected from the group consisting of aspartic acid, arginine, asparagine, cysteine, lysine, threonine, and serine, and wherein the active agent is attached to the side chain of the amino acid to form an amide, a thioester, an ester, an ether, a urethane, a carbonate, an anhydride or a carbamate. In yet another preferred embodiment, the glutamic acid is replaced by a synthetic amino acid with a pendant group comprising an amine, an alcohol, a sulfhydryl, an amide, a urea, or an acid functionality.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. Included in the drawing are the following figures.

DETAILED DESCRIPTION OF INVENTION

Figure 1:
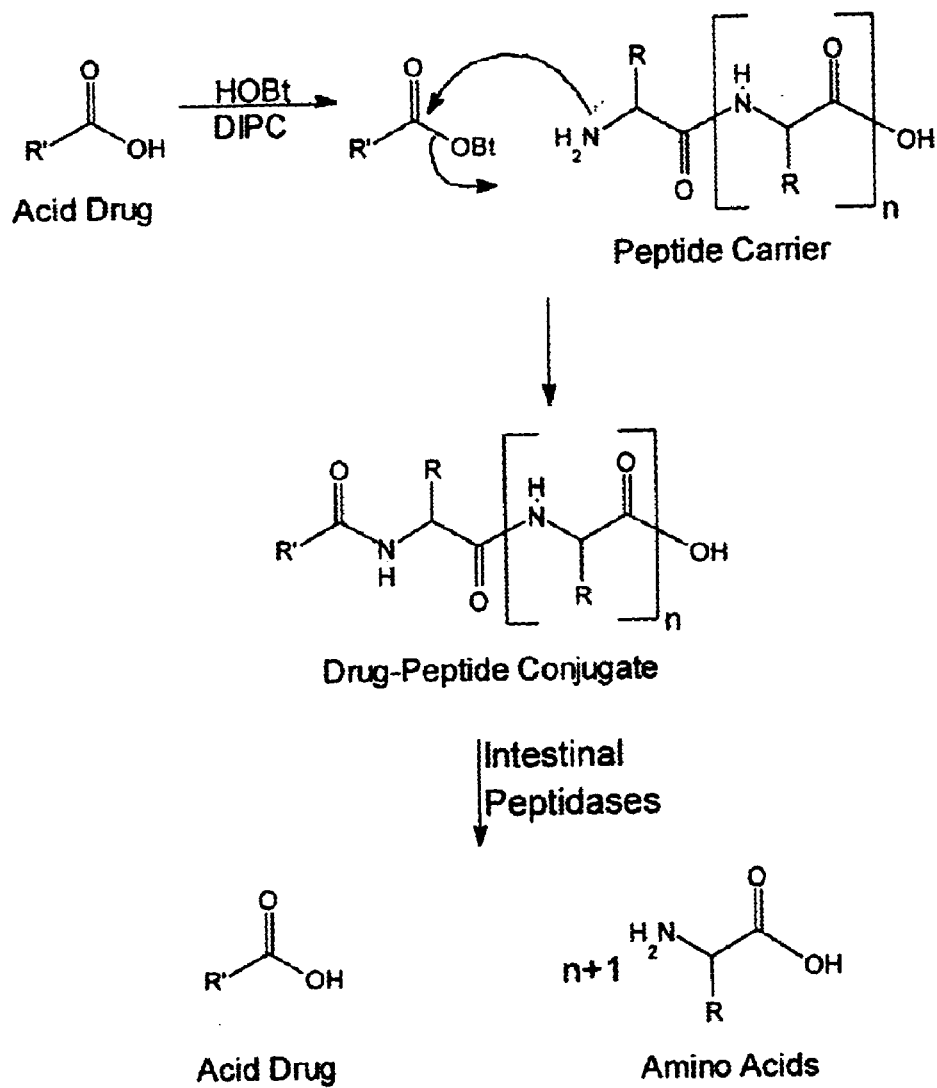
FIG. 1 illustrates an acid active agent/N-terminus scheme of the invention.

The present invention provides several benefits for active agent delivery. First, the invention can stabilize the active agent and prevent digestion in the stomach. In addition, the pharmacologic effect can be prolonged by delayed release of the active agent. Furthermore, active agents can be combined to produce synergistic effects. Also, absorption of the active agent in the intestinal tract can be enhanced. The invention also allows targeted delivery of active agents to specifics sites of action.

The composition of the invention comprises a polypeptide and an active agent covalently attached to the polypeptide. Preferably, the polypeptide is (i) an oligopeptide, (ii) a homopolymer of one of the twenty naturally occurring amino acids, (iii) a heteropolymer of two or more naturally occurring amino acids, (iv) a homopolymer of a synthetic amino acid, (v) a heteropolymer of two or more synthetic amino acids or (vi) a heteropolymer of one or more naturally occurring amino acids and one or more synthetic amino acids.

Proteins, oligopeptides and polypeptides are polymers of amino acids that have primary, secondary and tertiary structures. The secondary structure of the protein is the local conformation of the polypeptide chain and consists of helices, pleated sheets and turns. The protein's amino acid sequence and the structural constraints on the conformations of the chain determine the spatial arrangement of the molecule. The folding of the secondary structure and the spatial arrangement of the side chains constitute the tertiary structure.

Proteins fold because of the dynamics associated between neighboring atoms on the protein and solvent molecules. The thermodynamics of protein folding and unfolding are defined by the free energy of a particular condition of the protein that relies on a particular model. The process of protein folding involves, amongst other things, amino acid residues packing into a hydrophobic core. The amino acid side chains inside the protein core occupy the same volume as they do in amino acid crystals. The folded protein interior is therefore more like a crystalline solid than an oil drop and so the best model for determining forces contributing to protein stability is the solid reference state.

The major forces contributing to the thermodynamics of protein folding are Van der Waals interactions, hydrogen bonds, electrostatic interactions, configurational entropy and the hydrophobic effect. Considering protein stability, the hydrophobic effect refers to the energetic consequences of removing a polar groups from the protein interior and exposing them to water. Comparing the energy of amino acid hydrolysis with protein unfolding in the solid reference state, the hydrophobic effect is the dominant force. Hydrogen bonds are established during the protein fold process and intramolecular bonds are formed at the expense of hydrogen bonds with water. Water molecules are "pushed out" of the packed, hydrophobic protein core. All of these forces combine and contribute to the overall stability of the folded protein where the degree to which ideal packing occurs determines the degree of relative stability of the protein. The result of maximum packing is to produce a center of residues or hydrophobic core that has maximum shielding from solvent.

Since it is likely that lipophilic drugs would reside in the hydrophobic core of a peptide, it would require energy to unfold the peptide before the drug can be released. The unfolding process requires overcoming the hydrophobic effect by hydrating the amino acids or achieving the melting temperature of the protein. The heat of hydration is a destabilization of a protein. Typically, the folded state of a protein is favored by only 5–15 kcal/mole over the unfolded state. Nonetheless, protein unfolding at neutral pH and at room temperature requires chemical reagents. In fact, partial unfolding of a protein is often observed prior to the onset of irreversible chemical or conformation processes. Moreover, protein conformation generally controls the rate and extent of deleterious chemical reactions.

Conformational protection of active agents by proteins depends on the stability of the protein's folded state and the thermodynamics associated with the agent's decomposition. Conditions necessary for the agent's decomposition should be different than for protein unfolding.

Selection of the amino acids will depend on the physical properties desired. For instance, if increase in bulk or lipophilicity is desired, then the carrier polypeptide will be enriched in the amino acids in the table provided below. Polar amino acids, on the other hand, can be selected to increase the hydrophilicity of the polypeptide.

Ionizing amino acids can be selected for pH controlled peptide unfolding. Aspartic acid, glutamic acid and tyrosine carry a neutral charge in the stomach, but will ionize upon entry into the intestine. Conversely, basic amino acids, such as histidine, lysine and arginine, ionize in the stomach and are neutral in an alkaline environment.

Other factors such as π—π interactions between aromatic residues, kinking of the peptide chain by addition of proline, disulfide crosslinking and hydrogen bonding can all be used to select the optimum amino acid sequence for a given application. Ordering of the linear sequence can influence how these interactions can be maximized and is important in directing the secondary and tertiary structures of the polypeptide.

Furthermore, amino acids with reactive side chains (e.g., glutamic acid, lysine, aspartic acid, serine, threonine and cysteine) can be incorporated for attaching multiple active agents or adjuvants to the same carrier peptide. This is particularly useful if a synergistic effect between two or more active agents is desired.

As stated above, variable molecular weights of the carrier compound can have profound effects on the active agent release kinetics. As a result, low molecular weight active agent delivery systems are preferred. An advantage of this invention is that chain length and molecular weight of the polypeptide can be optimized depending on the level of conformational protection desired. This property can be optimized in concert with the kinetics of the first order release mechanism. Thus, another advantage of this invention is that prolonged release time can be imparted by increasing the molecular weight of the carrier polypeptide. Another, significant advantage of the invention is that the kinetics of active agent release is primarily controlled by the enzymatic hydrolysis of the key bond between the carrier peptide and the active agent.

Dextran is the only polysaccharide known that has been explored as a macromolecular carrier for the covalent binding of drug for colon specific drug delivery. Generally, it was only possible to load up to 1/10 of the total drug-dextran conjugate weight with drug. As stated earlier, polysaccharides are digested mainly in the colon and drug absorption is mainly limited to the colon. As compared to dextran, this invention has two major advantages. First, peptides are hydrolyzed by any one of several aminopeptidases found in the intestinal lumen or associated with the brush-border membrane and so active agent release and subsequent absorption can occur in the jejunum or the ileum. Second, the molecular weight of the carrier molecule can be controlled and, thus, active agent loading can also be controlled.

As a practical example, the following table lists the molecular weights of lipophilic amino acids (less one water molecule) and selected analgesics and vitamins.

TABLE

| Amino acid | MV | Active agent | MW |
|---|---|---|---|
| Glycine | 57 | Acetaminophen | 151 |
| Alanine | 71 | Vitamin B6 (Pyroxidine) | 169 |
| Valine | 99 | Vitamin C (Ascorbic acid) | 176 |
| Leucine | 113 | Aspirin | 180 |
| Isoleucine | 113 | Ibuprofen | 206 |
| Phenylalanine | 147 | Retinoic acid | 300 |
| Tyrosine | 163 | Vitamin $B_2$ (Riboflavin) | 376 |
| | | Vitamin $D_2$ | 397 |
| | | Vitamin E (Tocopherol) | 431 |

Lipophilic amino acids are preferred because conformational protection through the stomach is important for the selected active agents, which were selected based on ease of covalent attachment to an oligopeptide. Eighteen was subtracted from the amino acid's molecular weight so that their condensation into a polypeptide is considered. For example, a decamer of glycine (MW=588) linked to aspirin would have a total molecular weight of 750 and aspirin would represent 24% of the total weight of the active agent delivery composition or over two times the maximum drug loading for dextran. This is only for an N- or C- terminus application, for those active agents attached to pendant groups of decaglutamic acid, for instance, a drug with a molecular weight of 180 could conceivably have a loading of 58%, although this may not be entirely practical.

Figure 2:
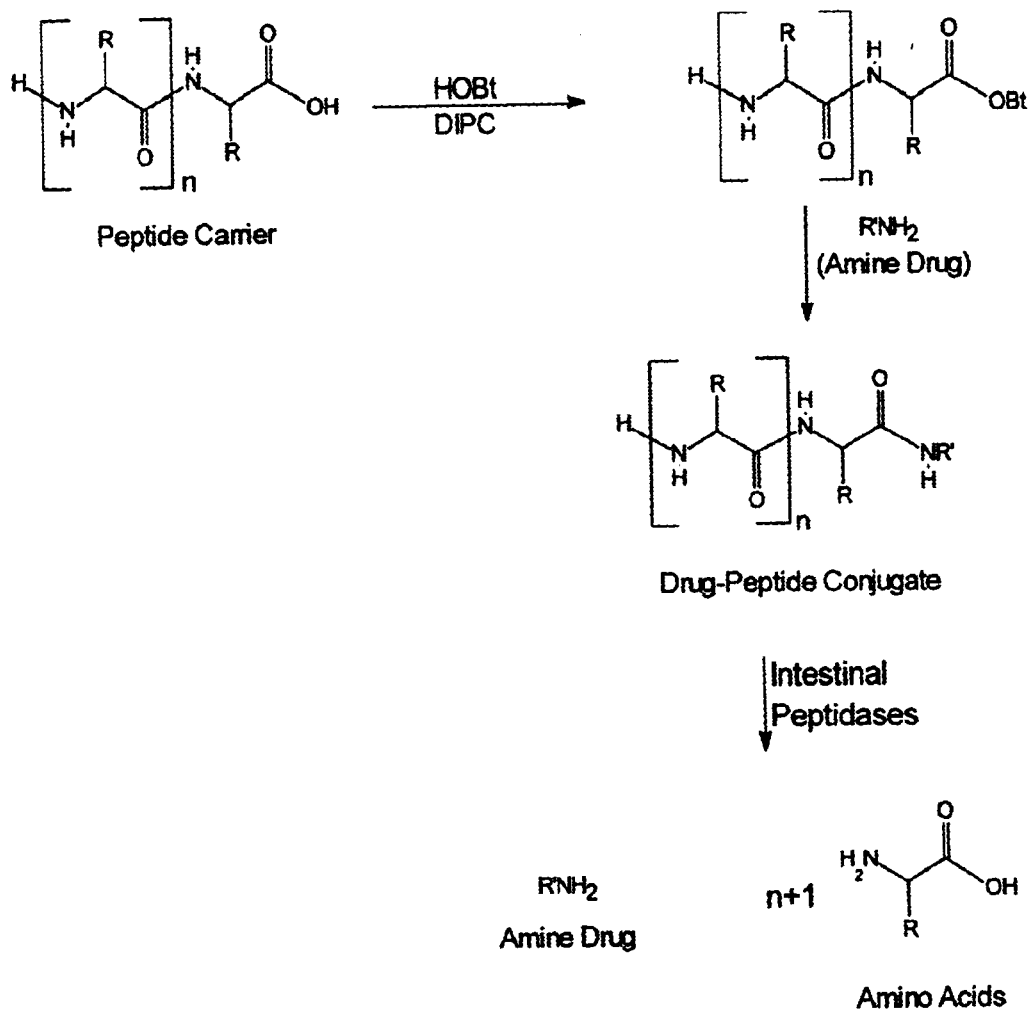
FIG. 2 illustrates an amine active agent/C-terminus scheme of the invention.
Figure 3:
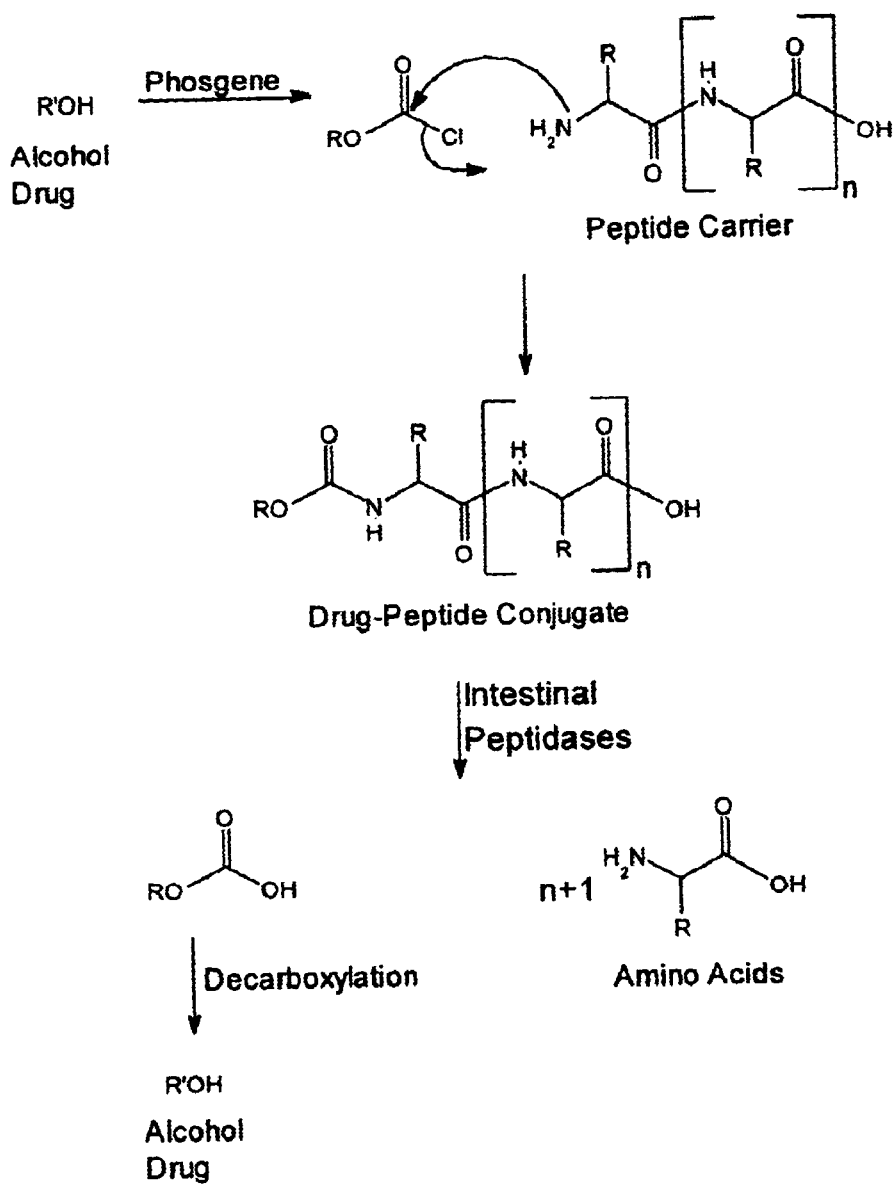
FIG. 3 illustrates an alcohol active agent/N-terminus scheme of the invention.

The alcohol, amine or carboxylic acid group of the active agent is covalently attached to the N-terminus, the C-terminus or the side chain of the oligopeptide or polypeptide. The location of attachment depends somewhat on the functional group selection. For instance, if the active drug is a carboxylic acid (e.g., aspirin) then the N-terminus of the oligopeptide is the preferred point of attachment as shown in FIG. 1. If the active agent is an amine (e.g., ampicillin), then the C-terminus is the preferred point of attachment in order to achieve a stable peptide linked active agent as shown in FIG. 2. In both, the C- and N-terminus examples, the peptide is, in essence, extended by one monomeric unit forming a new peptide bond. If the active agent is an alcohol, then either the C-terminus or the N-terminus is the preferred point of attachment in order to achieve a stable composition. As in the example above where the alcohol, norethindrone, was covalently attached to poly(hydroxypropylglutamine), an alcohol can be converted into an alkylchloroformate with phosgene. This invention, then, pertains to the reaction of this key intermediate with the N-terminus of the peptide carrier as shown in FIG. 3. FIGS. 1 through 3 also depict the release of the active ingredient from the peptide carrier by intestinal peptidases.

Figure 4:
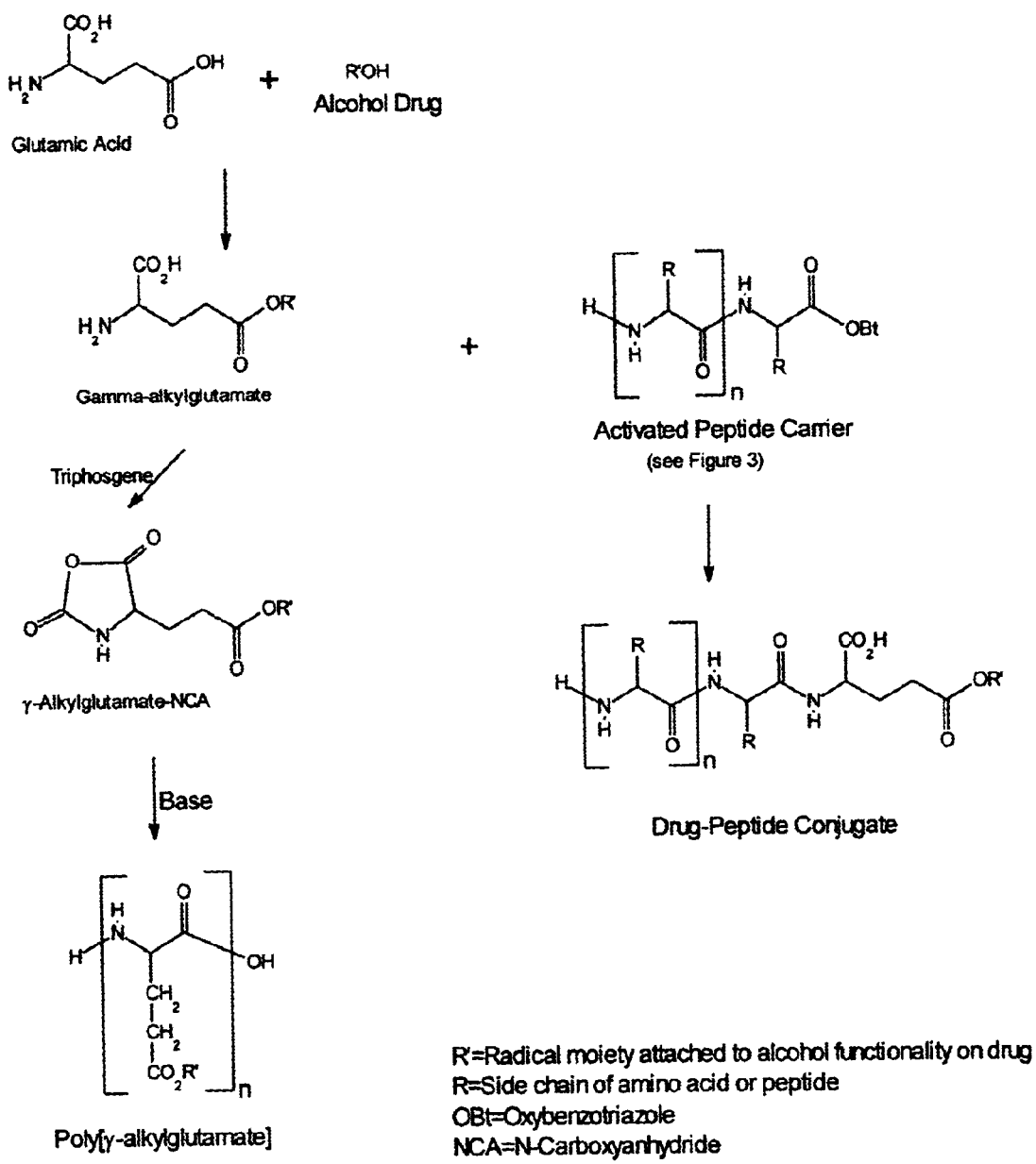
FIG. 4 illustrates an alcohol active agent/glutamic acid dimer preparation and conjugation scheme of the invention.
Figure 5:
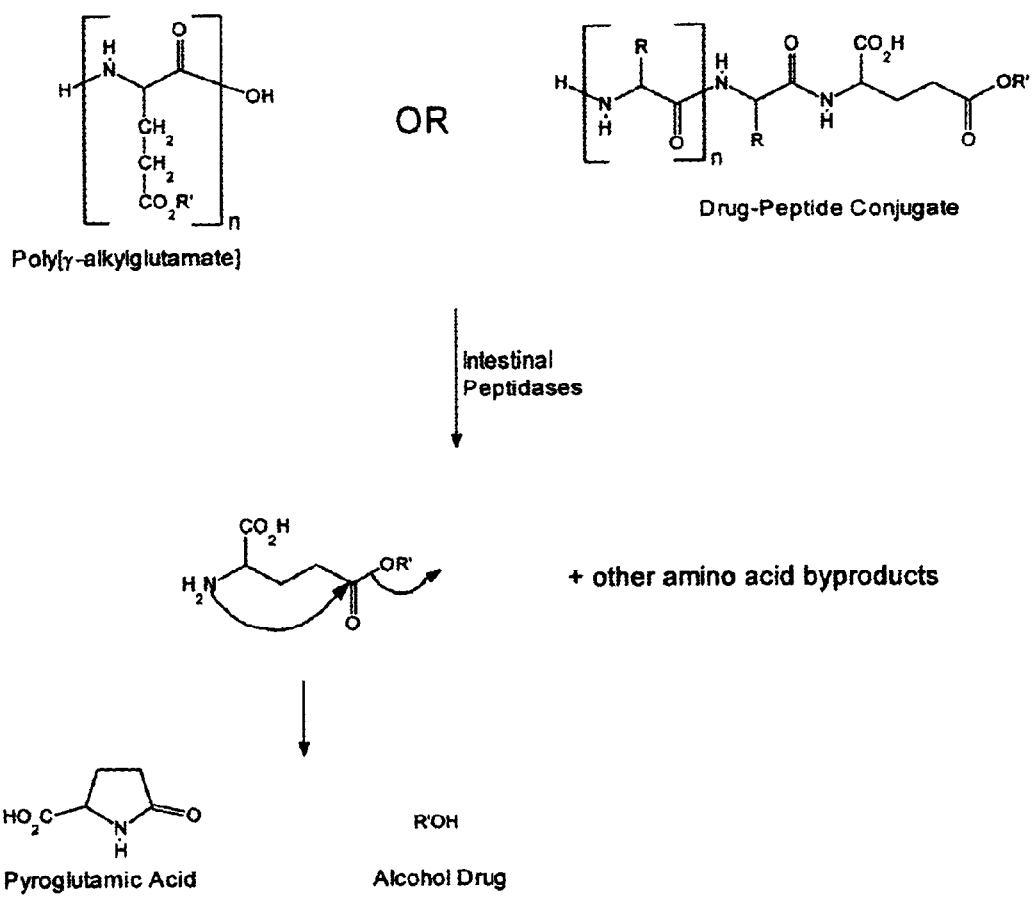
FIG. 5 illustrates a mechanism of alcohol active agent from glutamic acid dimer scheme.

The alcohol can be selectively bound to the gamma carboxylate of glutamic acid and then this conjugate covalently attached to the C-terminus of the peptide carrier. Because the glutamic acid-drug conjugate can be considered a dimer, this product adds two monomeric units to the C-terminus of the peptide carrier where the glutamic acid moiety serves as a spacer between the peptide and the drug as shown in FIG. 4. Intestinal enzymatic hydrolysis of the key peptide bond releases the glutamic acid-drug moiety from the peptide carrier. The newly formed free amine of the glutamic acid residue will then undergo an intramolecular transamination reaction, thereby, releasing the active agent with coincident formation of pyroglutamic acid as shown in FIG. 5. Alternatively, the glutamic acid-drug dimer can be converted into the gamma ester of glutamic acid N-carboxyanhydride. This intermediate can then be polymerized, as described above, using any suitable initiator as shown in FIG. 4. The product of this polymerization is polyglutamic acid with active ingredients attached to multiple pendant groups. Hence, maximum drug loading of the carrier peptide can be achieved. In addition, other amino acid-NCA's can be copolymerized with the gamma ester glutamic acid NCA to impart specific properties to the drug delivery system.

The invention also provides a method of imparting the same mechanism of action for other polypeptides containing functional side chains. Examples include, but are not limited to, polylysine, polyasparagine, polyarginine, polyserine, polycysteine, polytyrosine, polythreonine and polyglutamine. The mechanism can translate to these polypeptides through a spacer or linker on the pendant group, which is terminated, preferably, by the glutamic acid-drug dimer. This carrier peptide-drug conjugate is distinguished from the prior art by virtue of the fact that the primary release of the drug moiety relies on peptidases and not on esterases. Alternatively, the active agent can be attached directly to the pendant group where some other indigenous enzymes in the alimentary tract can affect release.

The active agent can be covalently attached to the N-terminus, the C-terminus or the side chain of the polypeptide using known techniques. Examples of linking organic compounds to the N-terminus type of a peptide include, but are not limited to, the attachment of naphthylacetic acid to LH-RH, coumarine acid to opioid peptides and 1,3-dialkyl-3-acyltriazenes to tetragastrin and pentagastrin. As another example, there are known techniques for forming peptide linked biotin and peptide linked acridine.

The polypeptide carrier can be prepared using conventional techniques. A preferred technique is copolymerization of mixtures of amino acid N-carboxyanhydrides. Alternatively, if a specific sequence is desired, a solid state automated peptide synthesizer can be used.

The addition of stabilizers to the composition has the potential of stabilizing the polypeptide further. Stabilizers such as sugar, amino acids, polyethylene glycol (PEG) and salts have been shown to prevent protein unfolding. In another embodiment of the invention, a pre-first order release of the active agent is imparted by microencapsulating the carrier polypeptide-active agent conjugate in a polysaccharide, amino acid complex, PEG or salts.

There is evidence that hydrophilic compounds are absorbed through the intestinal epithelia efficiently via specialized transporters. The entire membrane transport system is intrinsically asymmetric and responds asymmetrically to cofactors. Thus, one can expect that excitation of the membrane transport system will involve some sort of specialized adjuvant resulting in localized delivery of active agents. There are seven known intestinal transport systems classified according to the physical properties of the transported substrate. They include the amino acid, oligopeptide, glucose, monocarboxic acid, phosphate, bile acid and the P-glycoprotein transport systems and each has its own associated mechanism of transport. The mechanisms can depend on hydrogen ions, sodium ions, binding sites or other cofactors. The invention also allows targeting the mechanisms for intestinal epithelial transport systems to facilitate absorption of active agents.

In another embodiment of the invention, the composition includes one or more adjuvants to enhance the bioavailability of the active agent. Addition of an adjuvant is particularly preferred when using an otherwise poorly absorbed active agent. Suitable adjuvants, for example, include: papain, which is a potent enzyme for releasing the catalytic domain of aminopeptidase-N into the lumen; glycorecognizers, which activate enzymes in the BBM; and bile acids, which have been attached to peptides to enhance absorption of the peptides.

Preferably, the resultant peptide-active agent conjugate is formulated into a tablet using suitable excipients and can either be wet granulated or dry compressed.

Compositions of the invention are, in essence, the formation of amides from acids and amines and can be prepared by the following examples.

Acid/N-terminus Conjugation (FIG. 1)

An acid bioactive agent can be dissolved in DMF under nitrogen and cooled to 0° C. The solution can then be treated with diisopropylcarbodiimide and hydroxybenzotriazole followed by the amine peptide carrier. The reaction can then be stirred for several hours at room temperature, the urea by-product filtered off, the product precipitated out in ether and purified using gel permeation chromatography (GPC) or dialysis.

Amine/C-terminus Conjugation (FIG. 2)

The peptide carrier can be dissolved in DMF under nitrogen and cooled to 0° C. The solution can then be treated with diisopropylcarbodiimide and hydroxybenzotriazole followed by the amine bioactive agent. The reaction can then be stirred for several hours at room temperature, the urea by-product filtered off, the product precipitated out in ether and purified using GPC or dialysis.

Alcohol/N-Terminus Conjugation (FIG. 3)

In the following example the combination of the alcohol with triphosgene produces a chloroformate, which when reacted with the N-terminus of the peptide produces a carbamate. Pursuant to this, an alcohol bioactive agent can be treated with triphosgene in dry DMF under nitrogen. The suitably protected peptide carrier is then added slowly and the solution stirred at room temperature for several hours. The product is then precipitated out in ether. The crude product is suitably deprotected and purified using GPC.

Other solvents, activating agents, cocatalysts and bases can be used. Examples of other solvents include dimethylsulfoxide, ethers such as tetrahydrofuran or chlorinated solvents such as chloroform. Examples of other activating agents include dicyclohexylcarbodiimide or thionyl chloride. An example of another cocatalyst is N-hydroxysuccinimide. Examples of bases include pyrrolidinopyridine, dimethylaminopyridine, triethylamine or tributylamine.

Preparation of γ-Alkyl Glutamate (FIG. 4)

There have been over 30 different γ-alkyl glutamates prepared any one of which may be suitable for the drug alcohol of choice. For example, a suspension of glutamic acid, the alcohol and concentrated hydrochloric acid can be prepared and heated for several hours. The γ-alkyl glutamate product can be precipitated out in acetone, filtered, dried and recrystallized from hot water.

γ-Alkyl Glutumate/C-Terminus Conjugation (FIG. 4)

The peptide carrier can be dissolved in DMP under nitrogen and cooled to 0° C. The solution can then be treated with diisopropylcarbodiimide and hydroxybenzotriazole followed by the γ-alkyl glutamate bioactive agent. The reaction can then be stirred for several hours at room temperature, the urea by-product filtered off, the product precipitated out in ether and purified using GPC or dialysis.

Preparation of γ-Alkyl Glutamate-NCA

γ-Alkyl glutamate can be suspended in dry THF where triphosgene is added and the mixture refluxed under a nitrogen atmosphere until the mixture becomes homogenous. The solution can be poured into heptane to precipitate the NCA product, which is filtered, dried and recrystallized from a suitable solvent.

Preparation of Poly[γ-Alkyl Glutamate]

γ-Alkyl glutamate-NCA can be dissolved in dry DMF where a catalytic amount of a primary amine can be added to the solution until it becomes viscous (typically overnight). The product can be isolated from the solution by pouring it into water and filtering. The product can be purified using GPC or dialysis.

Although illustrated and described above with reference to specific embodiments, the invention is nevertheless not intended to be limited to the details shown. Rather, various modifications may be made in the details within the scope and range of equivalents of the claims and without departing from the spirit of the invention.

What is claimed is:

1. A composition comprising:
    a polypeptide wherein said polypeptide is a heteropolymer of two or more synthetic amino acids;
    an active agent covalently attached to the side chain of said polypeptide; and wherein said composition is in a form suitable for oral administration and release of said active agent into the bloodstream following oral administration.

2. A composition comprising:
    a polypeptide;
    an active agent other than an amino acid wherein said active agent is an amine and wherein said active agent is covalently attached through said amine to the C-terminus of said polypeptide; and
    wherein said composition is in a form suitable for oral administration and enzymatic release of said active agent into the bloodstream following oral administration.

3. A composition comprising:
    a polypeptide;
    an active agent wherein said active agent is an alcohol and wherein said active agent is covalently attached through said alcohol to the C-terminus of said polypeptide; and
    wherein said composition is in a form suitable for oral administration and enzymatic release of said active agent into the bloodstream following oral administration.

4. A composition comprising:
    a polypeptide;
    an active agent wherein said active agent is an alcohol and wherein said active agent is covalently attached through said alcohol to the N-terminus of said polypeptide; and
    wherein said composition is in a form suitable for oral administration and enzymatic release of said active agent into the bloodstream following oral administration.

5. A method for delivering an active agent to a patient comprising administering to said patient a composition comprising:
    a polypeptide wherein said polypeptide is covalently attached to an adjuvant wherein said adjuvant is not an amino acid;
    an active agent other than an amino acid covalently attached to said polypeptide;
    wherein said composition is in a form suitable for oral administration and release of said active agent into the bloodstream following oral administration; and
    wherein release of said adjuvant from said composition is controlled by said polypeptide.

6. A composition comprising:
    a polypeptide wherein said polypeptide consists of one or more of the twenty naturally occurring amino acids,
    an active agent other than an amino acid wherein said active agent is an amine and wherein said active agent is covalently attached through said amine to the C-terminus of said polypeptide; and wherein said composition is in a form suitable for oral administration and enzymatic release of said active agent into the bloodstream following oral administration.

7. A composition comprising:
a polypeptide wherein said polypeptide consists of one or more of the twenty naturally occurring amino acids,
an active agent wherein said active agent is an alcohol which is covalently attached through said alcohol to the C-terminus of said polypeptide; and
wherein said composition is in a form suitable for oral administration and enzymatic release of said active agent into the bloodstream following oral administration.

8. A composition comprising:
a polypeptide wherein said polypeptide consists of one or more of the twenty naturally occurring amino acids,
an active agent wherein said active agent is an alcohol which is covalently attached through said alcohol to the N-terminus of said polypeptide; and
wherein said composition is in a form suitable for oral administration and enzymatic release of said active agent into the bloodstream following oral administration.

9. A composition comprising:
a polypeptide;
an active agent other than an amino acid wherein said active agent is an alcohol covalently attached to said polypeptide through said alcohol in a form suitable for oral administration and enzymatic release of said active agent into the bloodstream following oral administration wherein said composition is in the form of an ingestible tablet, a capsule, or an oral suspension.

10. The composition of claim 9 wherein said polypeptide consists of one or more of the twenty naturally occurring amino acids.

11. The composition of claim 9, wherein said polypeptide consists of one or more amino acids selected from glutamic acid, aspartic acid, arginine, asparagine, cysteine, lysine, threonine, or serine.

12. The composition of claim 11, wherein the polypeptide consists of glutamic acid.

13. The composition of claim 11, wherein the polypeptide consists of serine.

14. The composition of claim 11, wherein the polypeptide consists of lysine.

15. The composition of claims 9, 10, 11, 12, 13 or 14 wherein said active agent is attached through the C-terminus.

16. The composition of claims 9, 10, 11, 12, 13 or 14 wherein said active agent is attached through the N-terminus.

17. The composition of claims 9, 10, 11, 12, 13 or 14 wherein said active agent is attached through the side chain of an amino acid.

18. A composition comprising:
a polypeptide;
an active agent other than an amino acid wherein said active agent is an amine covalently attached to said polypeptide through said amine in a form suitable for oral administration and enzymatic release of said active agent into the bloodstream following oral administration wherein said composition is in the form of an ingestible tablet, a capsule or an oral suspension.

19. The composition of claim 18, wherein said polypeptide consists of one or more of the twenty naturally occurring amino acids.

20. The composition of claim 18, wherein said polypeptide consists of one or more amino acids selected from glutamic acid, aspartic acid, arginine, asparagine, cysteine, lysine, threonine, and serine.

21. The composition of claim 20, wherein the polypeptide consists of glutamic acid.

22. The composition of claim 20, wherein the polypeptide consists of serine.

23. The composition of claim 20, wherein the polypeptide consists of lysine.

24. The composition of claims 18, 19, 20, 21, 22, or 23 wherein said active agent is attached through the C-terminus.

25. The composition of claims 18, 19, 20, 21 or 22 wherein said active agent is attached through the side chain of an amino acid.

26. A composition comprising:
a polypeptide;
an active agent other than an amino acid wherein said active agent is a carboxylic acid covalently attached to said polypeptide through said carboxylic acid in a form suitable for oral administration and enzymatic release of said active agent into the bloodstream following oral administration wherein said composition is in the form of an ingestible tablet, a capsule, or an oral suspension.

27. The composition of claim 26, wherein said polypeptide consists of one or more of the twenty naturally occurring amino acids.

28. The composition of claim 26, wherein said polypeptide consists of one or more amino acids selected from glutamic acid, aspartic acid, arginine, asparagine, cysteine, lysine, threonine, and serine.

29. The composition of claim 28, wherein the polypeptide consists of glutamic acid.

30. The composition of claim 28, wherein the polypeptide consists of serine.

31. The composition of claim 28, wherein the polypeptide consists of lysine.

32. The composition of claims 26, 27, 28, 29, 30, or 31 wherein said active agent is attached through the N-terminus.

33. The composition of claims 26, 27, 28, 30, or 31 wherein said active agent is attached through the side chain of an amino acid.

34. A method for delivering an active agent to a patient comprising:
orally administering to said patient a composition comprising a polypeptide wherein the polypeptide consists of one or more of the twenty naturally occurring amino acids, covalently attached to an active agent other than an amino acid through an alcohol, an amine or a carboxylic acid functionality, in a form suitable for oral administration and enzymatic release of said active agent into the bloodstream following oral administration wherein said composition is in the form of an ingestible tablet, a capsule, or an oral suspension.

35. The method of claim 34, wherein said active agent is attached through the C-terminus.

36. The method of claim 35, wherein said active agent is an alcohol which is attached through a hydroxyl group.

37. The method of claim 35, wherein said active agent is an amine which is attached through an amine group.

38. The method of claim 34, wherein said active agent is attached through the N-terminus.

39. The method of claim 38, wherein said active agent is an alcohol which is attached through a hydroxyl group.

40. The method of claim 38, wherein said active agent is a carboxylic acid which is attached through an acid group.

41. The method of claim 34, wherein said active agent is attached through the side chain of an amino acid.

42. The method of claim 41, wherein said active agent is an alcohol which is attached through a hydroxyl group.

43. The method of claim 41, wherein said active agent is an amine which is attached through an amine group.

44. The method of claim 41, wherein said active agent is a carboxylic acid which is attached through an acid group.

45. The method of any one of claims 35–37, 39, or 40–44 wherein the polypeptide consists of glutamic acid.

46. The method of any one of claims 35–37, 39, or 40–44 wherein the polypeptide consists of serine.

47. The method of any one of claims 35–37, 39, or 40–44, wherein the polypeptide consists of lysine.

48. A composition comprising:
   a polypeptide wherein said polypeptide is a heteropolymer of two or more synthetic amino acids;
   an active agent other than an amino acid covalently attached to said polypeptide; and wherein said composition is in a form suitable for oral administration and enzymatic release of said active agent into the bloodstream following oral administration wherein said composition is in the form of an ingestible tablet, a capsule, or an oral suspension.

49. Composition of claim 48, wherein said active agent is attached to the N-terminus.

50. Composition of claim 48, wherein said active agent is attached to the C-terminus.

51. Composition of claim 48, wherein said active agent is attached to the side chain.

52. A composition comprising:
   a polypeptide;
   an active agent other than an amino acid covalently attached to said polypeptide in a form suitable for oral administration and enzymatic release of said active agent into the bloodstream following oral administration wherein said composition is in the form of an ingestible tablet, a capsule, or an oral suspension.

53. The composition of claim 52, wherein said polypeptide comprises one or more of the twenty naturally occurring amino acids.

54. The composition of claim 52, wherein said polypeptide comprises glutamic acid, aspartic acid, arginine, asparagine, cysteine, lysine, threonine, or serine.

55. The composition of claim 54, wherein the polypeptide comprises glutamic acid.

56. The composition of claim 54, wherein the polypeptide comprises serine.

57. The composition of claim 54, wherein the polypeptide comprises lysine.

58. The composition of claims 52, 53, 54, 55, 56, or 57 wherein said active agent is attached through the C-terminus.

59. The composition of claims 52, 53, 54, 55, 56, or 57 wherein said active agent is attached through the N-terminus.

60. The composition of claims 52, 53, 54, 55, 56, or 57 wherein said active agent is attached through the side chain of an amino acid.

61. A composition comprising:
   a polypeptide consisting essentially of one or more of the twenty naturally occurring amino acids;
   an active agent other than an amino acid covalently attached to said polypeptide in a form suitable for oral administration and enzymatic release of said active agent into the bloodstream following oral administration wherein said composition is in the form of an ingestible tablet, a capsule, or an oral suspension.

62. The composition of claim 61, wherein said naturally occurring amino acid is glutamic acid.

63. The composition of claim 61, wherein said naturally occurring amino acid is lysine.

64. The composition of claim 61, wherein said naturally occurring amino acid is serine.

* * * * *

UNITED STATES PATENT AND TRADEMARK OFFICE
CERTIFICATE OF CORRECTION

PATENT NO. : 6,716,452 B1
DATED : April 6, 2004
INVENTOR(S) : Piccariello et al.

It is certified that error appears in the above-identified patent and that said Letters Patent is hereby corrected as shown below:

Title page,
Item [56], References Cited, OTHER PUBLICATIONS, delete reference "Presentation to Knoll" through reference "Feb. 10, 2000 Lotus Presentation."

Signed and Sealed this

Thirtieth Day of November, 2004

JON W. DUDAS
*Director of the United States Patent and Trademark Office*